United States Patent
Mazzoleni et al.

(10) Patent No.: US 11,564,439 B2
(45) Date of Patent: Jan. 31, 2023

(54) SYSTEM AND METHOD FOR DETERMINING FOOT STRIKE PATTERN

(71) Applicant: Under Armour, Inc., Baltimore, MD (US)

(72) Inventors: Michael Mazzoleni, Baltimore, MD (US); F. Grant Kovach, Baltimore, MD (US); Jeffrey Allen, Baltimore, MD (US); Christopher Green, Baltimore, MD (US)

(73) Assignee: Under Armour, Inc., Baltimore, MD (US)

( * ) Notice: Subject to any disclaimer, the term of this patent is extended or adjusted under 35 U.S.C. 154(b) by 761 days.

(21) Appl. No.: 16/529,093

(22) Filed: Aug. 1, 2019

(65) Prior Publication Data
US 2020/0046061 A1  Feb. 13, 2020

Related U.S. Application Data

(60) Provisional application No. 62/715,344, filed on Aug. 7, 2018.

(51) Int. Cl.
*A43B 3/34* (2022.01)
*A63B 24/00* (2006.01)
(Continued)

(52) U.S. Cl.
CPC .................. *A43B 3/34* (2022.01); *A43B 3/44* (2022.01); *A61B 5/1118* (2013.01); *A61B 5/681* (2013.01);
(Continued)

(58) Field of Classification Search
CPC .......... A43B 3/34; A43B 3/44; A61B 5/1118; A61B 5/6807; A61B 5/681; A61B 5/1112;
(Continued)

(56) References Cited

U.S. PATENT DOCUMENTS 10,251,446 B2 *  4/2019  Bischoff ................ A43B 13/14
11,016,111 B1 *  5/2021  Chuang ................ A61B 5/6807
(Continued)

OTHER PUBLICATIONS

Giandolini, M., et al., A Simple Field Method to Identify Foot Strike Pattern During Running, Journal of Biomechanics, 2014.
(Continued)

*Primary Examiner* — Omar Casillashernandez
(74) *Attorney, Agent, or Firm* — Maginot, Moore & Beck, LLP

(57) ABSTRACT

A fitness tracking system includes a shoe, a monitoring device, and a controller. The monitoring device is mounted on the shoe and includes an accelerometer configured to generate acceleration data corresponding to acceleration of a foot received by the shoe. The controller is operably connected to the accelerometer and is configured to collect sampled acceleration data by sampling the generated acceleration data, to identify foot strike data of the sampled acceleration data, to identify a local minimum of the sampled acceleration data collected prior to the foot strike data, and to determine foot strike characteristic data corresponding to the foot strike data based on an acceleration value at the local minimum.

20 Claims, 13 Drawing Sheets

(51) Int. Cl.
  *A61B 5/11* (2006.01)
  *A61B 5/00* (2006.01)
  *A43B 3/44* (2022.01)
  *G06K 9/00* (2022.01)

(52) U.S. Cl.
  CPC ........ *A61B 5/6807* (2013.01); *A63B 24/0062* (2013.01); *G06K 9/0053* (2013.01); *A61B 5/1112* (2013.01); *A61B 2562/0219* (2013.01); *A63B 2024/0065* (2013.01); *A63B 2220/40* (2013.01); *A63B 2220/51* (2013.01); *A63B 2225/50* (2013.01)

(58) Field of Classification Search
  CPC .......... A61B 2562/0219; A61B 5/0022; A61B 5/112; A61B 5/1121; A63B 24/0062; A63B 2024/0065; A63B 2220/40; A63B 2220/51; A63B 2225/50; G06K 9/0053; G16H 40/67
  USPC .......................................... 434/247; 343/247
  See application file for complete search history.

(56) References Cited

U.S. PATENT DOCUMENTS

| | | | |
|---|---|---|---|
| 2007/0233403 A1* | 10/2007 | Alwan | A61B 5/1038 702/33 |
| 2009/0267783 A1* | 10/2009 | Vock | A43B 3/34 340/669 |
| 2013/0190658 A1* | 7/2013 | Flaction | A63B 24/0006 600/595 |
| 2016/0296412 A1* | 10/2016 | Thomas | A43B 7/144 |
| 2018/0263532 A1* | 9/2018 | Smulyan | A43B 17/00 |
| 2018/0279914 A1* | 10/2018 | Patek | G06K 9/00557 |
| 2018/0358119 A1* | 12/2018 | Bhushan | G16H 40/63 |
| 2019/0150793 A1* | 5/2019 | Barth | A61B 5/7267 |

OTHER PUBLICATIONS

Giandolini, M., et al., Foot Strike Pattern and Impact Continuous Measurements During a Trail Running Race: Proof of Concept in a World-Class Athlete, Footwear Science, Taylor & Francis, 2015.

Strohrmann, C., et al., Out of the Lab and Into the Woods: Kinematic Analysis in Running Using Wearable Sensors, ACM, 2011, Beijing.

Strohrmann, C., et al., Quantified Performance: Assessing runners with sensors, XRDS, 2013, vol. 20, No. 2, ACM.

Scribe: Wearable Gait Analysis System, https://runscribe.com/, available at least as early as Jul. 10, 2019.

\* cited by examiner

SYSTEM AND METHOD FOR DETERMINING FOOT STRIKE PATTERN

COPYRIGHT

This document claims priority to U.S. Provisional Patent Application Ser. No. 62/715,344, filed Aug. 7, 2018, the entire contents of which are incorporated herein by reference.

COPYRIGHT

A portion of the disclosure of this patent document contains material that is subject to copyright protection. The copyright owner has no objection to the facsimile reproduction by anyone of the patent document or the patent disclosure, as it appears in the Patent and Trademark Office patent files or records, but otherwise reserves all copyright rights whatsoever.

Field

This disclosure relates to the field of fitness tracking systems and in particular to processing movement data generated by a fitness tracking system to determine a foot strike pattern of a user.

Background

Active individuals, such as walkers, runners, and other athletes commonly use fitness tracking systems to collect and track activity data. For example, active individuals may utilize a fitness tracking system to determine metrics of interest including a distance traversed, a workout duration, and a workout intensity.

Another metric of interest to some users is foot strike pattern. Foot strike pattern corresponds to the first part of the user's foot or shoe to impact the ground at the end of a stride. A common foot strike pattern is a heel foot strike pattern, which means that the user's heel is the first part of the user's foot to impact the ground as the user completes a stride. Foot strike patterns range from the heel foot strike pattern to a forefoot foot strike pattern and include a midfoot foot strike pattern.

Known fitness tracking systems have attempted to detect the foot strike pattern of a user with a complicated arrangement of sensors attached to the user's shoes or to the user's legs. For example, some prior systems use a complicated pressure sensor arrangement attached to the user's shoes to determine the foot strike pattern. Known systems for determining foot strike pattern are complex, electrical power intensive, expensive, and do not produce results of sufficient accuracy for most users.

Based on the above, further developments in the determination of a user's foot strike pattern are desirable in order to improve the user experience of fitness tracking systems.

SUMMARY

According to an exemplary embodiment of the disclosure a fitness tracking system includes a shoe, a monitoring device, and a controller. The monitoring device is mounted on the shoe and includes an accelerometer configured to generate acceleration data corresponding to acceleration of a foot received by the shoe. The controller is operably connected to the accelerometer and is configured to collect sampled acceleration data by sampling the generated acceleration data, to identify foot strike data of the sampled acceleration data, to identify a local minimum of the sampled acceleration data collected prior to the foot strike data, and to determine foot strike characteristic data corresponding to the foot strike data based on an acceleration value at the local minimum.

According to another exemplary embodiment, a method of operating a fitness tracking system to determine foot strike characteristic data of a user of the fitness tracking system is disclosed. The method includes generating acceleration data with an acceleration sensor mounted to a foot of the user, the acceleration data corresponding to acceleration of the foot, collecting sampled acceleration data by sampling the generated acceleration data, and identifying foot strike data of the sampled acceleration data. The method further includes identifying a local minimum of the sampled acceleration data collected prior to the foot strike data, and determining foot strike characteristic data corresponding to the foot strike data based on an acceleration value at the local minimum.

According to yet another exemplary embodiment, a method of operating a fitness tracking system to determine foot strike characteristic data of a user of the fitness tracking system is disclosed. The method includes generating acceleration data with an acceleration sensor mounted to a foot of the user, the acceleration data corresponding to acceleration of the foot, collecting sampled acceleration data by sampling the generated acceleration data, identifying foot strike data of the sampled acceleration data, and determining foot strike characteristic data corresponding to the foot strike data based on acceleration data generated prior to the foot strike data.

BRIEF DESCRIPTION OF THE FIGURES

The above-described features and advantages, as well as others, should become more readily apparent to those of ordinary skill in the art by reference to the following detailed description and the accompanying figures in which.

All Figures © Under Armour, Inc. 2018. All rights reserved.

DETAILED DESCRIPTION

Disclosed embodiments include systems, apparatus, methods and storage medium associated with processing data generated by a fitness tracking system, which is also referred to herein as an activity tracking system.

Aspects of the disclosure are disclosed in the accompanying description. Alternate embodiments of the disclosure and their equivalents may be devised without parting from the spirit or scope of the disclosure. It should be noted that any description herein regarding "one embodiment," "an embodiment," "an exemplary embodiment," and the like indicate that the embodiment described may include a particular feature, structure, or characteristic, and that such particular feature, structure, or characteristic may not necessarily be included in every embodiment. In addition, references to the foregoing do not necessarily comprise a reference to the same embodiment. Finally, irrespective of whether it is explicitly described, one of ordinary skill in the art would readily appreciate that each of the particular features, structures, or characteristics of the given embodiments may be utilized in connection or combination with those of any other embodiment discussed herein.

Various operations may be described as multiple discrete actions or operations in turn, in a manner that is most helpful in understanding the claimed subject matter. However, the order of description should not be construed as to imply that these operations are necessarily order dependent. In particular, these operations may or may not be performed in the order of presentation. Operations described may be performed in a different order than the described embodiment. Various additional operations may be performed and/or described operations may be omitted in additional embodiments.

For the purposes of the present disclosure, the phrase "A and/or B" means (A), (B), or (A and B). For the purposes of the present disclosure, the phrase "A, B, and/or C" means (A), (B), (C), (A and B), (A and C), (B and C), or (A, B and C).

The terms "comprising," "including," "having," and the like, as used with respect to embodiments of the present disclosure, are synonymous.

Figure 1:
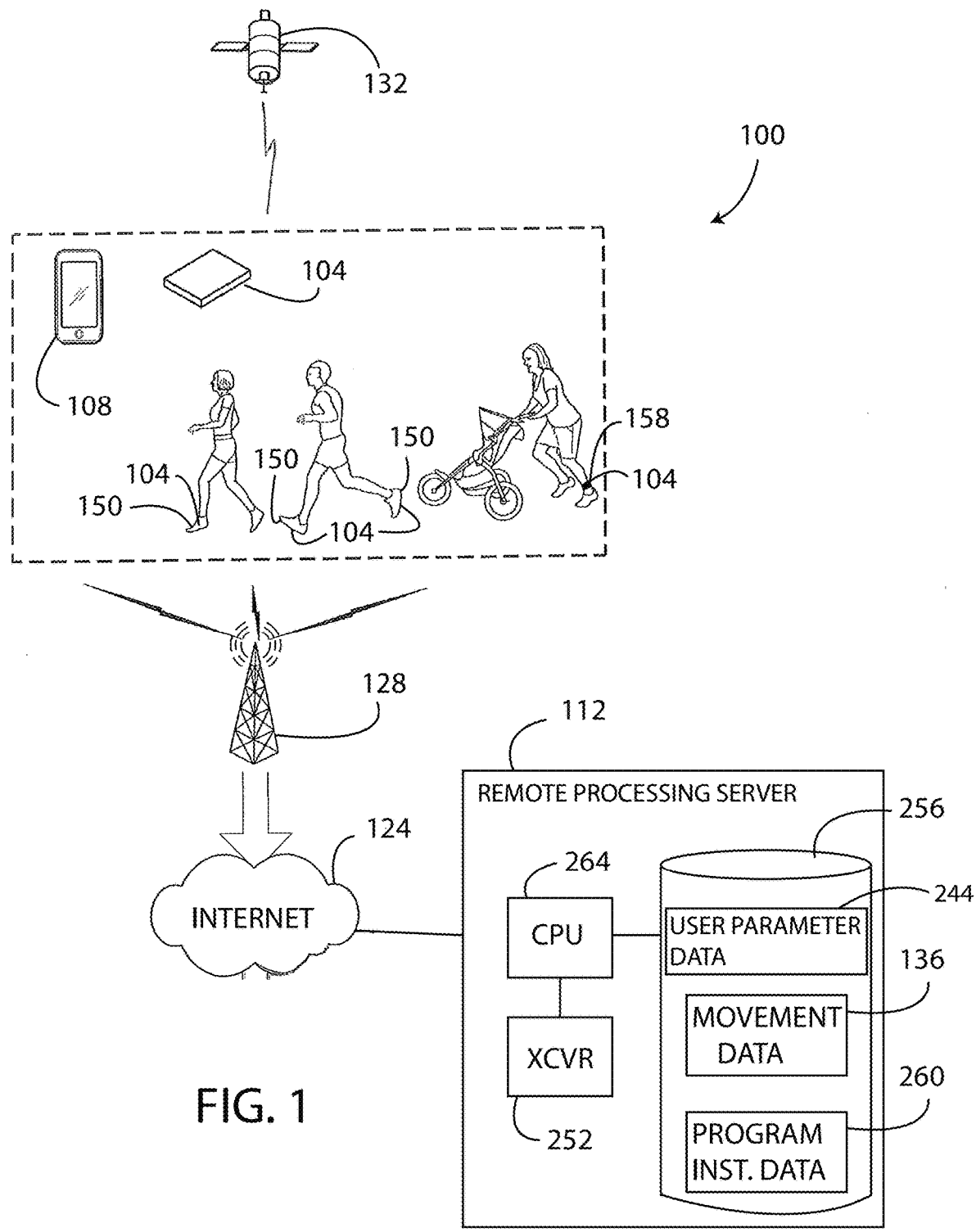
FIG. 1 is a block diagram of a fitness tracking system, as disclosed herein, that includes a monitoring device, a personal electronic device, and a remote processing server.

As shown in FIG. 1, a fitness tracking system 100 includes a monitoring device 104, a personal electronic device 108, and a remote processing server 112. The fitness tracking system 100 is configured to transmit and receive data over the Internet 124 using a cellular network 128, for example. The fitness tracking system 100 may also be configured for use with a global positioning system ("GPS") 132.

As disclosed herein, the fitness tracking system 100 generates movement data 136 corresponding to movement of the user. The fitness tracking system 100 processes the movement data 136 to determine foot strike characteristic data 200 (FIG. 2), which is indicative of the foot strike pattern of the user. The fitness tracking system 100 may also be configured to determine a level of fatigue of the user based on the movement data 136. Components of the fitness tracking system 100 and a method 800 (FIG. 8) for operating the fitness tracking system 100 are described herein.

The Monitoring Device

Figure 2:
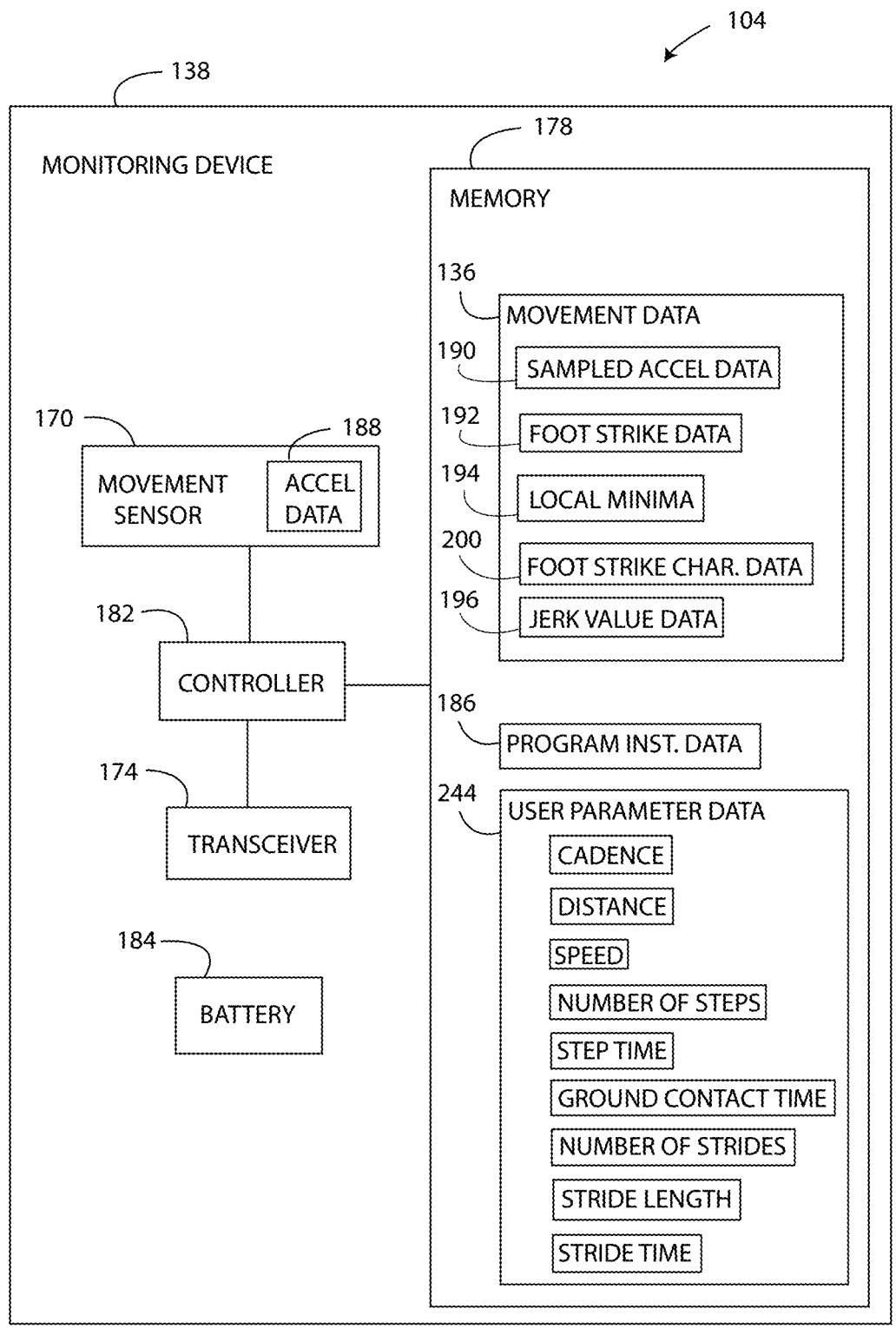
FIG. 2 is a block diagram of the monitoring device of FIG. 1.

As shown in FIG. 2, the monitoring device 104 includes a housing 138 configured to contain a movement sensor 170, a transceiver 174, and a memory 178 each of which is operably connected to a controller 182 and a battery 184. The monitoring device 104 is also referred to herein as a measuring device, a health parameter monitoring/measuring device, a distance monitoring/measuring device, a speed monitoring/measuring device, and/or an activity monitoring device.

The movement sensor 170 is provided as at least one of an accelerometer, a gyroscope, and a magnetometer that is configured to generate sensor data. In one embodiment, the movement sensor 170 includes an accelerometer configured to generate acceleration data 188 that corresponds to acceleration of the user along only a selected axis of movement. For example, the movement sensor 170 is provided as a single-axis microelectromechanical (MEMS) accelerometer configured to generate acceleration data 188 corresponding to acceleration of the user's foot along a vertical axis. In another embodiment, the movement sensor 170 includes a multi-axis accelerometer configured to generate sensor data that is (or includes) acceleration data 188 of the user's foot along more than one axis of movement, such as along two axes of movement or along three axes of movement. In a further embodiment, the movement sensor 170 includes a multi-axis accelerometer configured to generate sensor data that is (or includes) acceleration data 188 of the user's foot along only a selected axis of movement, which corresponds to the vertical axis. In this embodiment, the multi-axis accelerometer includes hardware for generating sensor data corresponding to more than one axis of movement, but the controller 182 configures the accelerometer to generate sensor data corresponding to only one axis of movement, as a means of limiting the electrical energy required to operate the monitoring device 104, for example.

As shown in FIG. 2, the transceiver 174 of the monitoring device 104, which is also referred to as a wireless transmitter and/or receiver, is configured to transmit and to receive data from the personal electronic device 108. In one embodiment, the transceiver 174 is configured for operation according to the Bluetooth® wireless data transmission standard. In other embodiments, the transceiver 174 comprises any desired transceiver configured to wirelessly transmit and receive data using a protocol including, but not limited to, Near Field Communication ("NFC"), IEEE 802.11, Global System for Mobiles ("GSM"), and Code Division Multiple Access ("CDMA").

The memory 178 of the monitoring device 104 is an electronic data storage unit, which is also referred to herein as a non-transient computer readable medium. The memory 178 is configured to store the movement data 136, program instruction data 186, user parameter data 244, and any other electronic data associated with the fitness tracking system 100. The program instruction data 186 includes computer executable instructions for operating the monitoring device 104. As described in further detail herein, the movement data 136 includes sampled acceleration data 190 based on the acceleration data 188, foot strike data 192, local minima data 194 corresponding to minima of the sampled acceleration data 190, jerk value data 196 of the sampled acceleration data 190, and the foot strike characteristic data 200 that corresponds to the foot strike pattern of the user as determined by the fitness tracking system 100.

The controller 182 of the monitoring device 104 is configured to execute the program instruction data 186 for controlling the movement sensor 170, the transceiver 174, and the memory 178. The controller 182 is configured as a microprocessor, a processor, or any other type of electronic control chip.

With continued reference to FIG. 2, the controller 182 is further configured to execute the program instruction data 186 to determine and/or calculate the user parameter data 244 by applying, for example, a set of rules to the movement data 136. The rules of the set of rules are categorized as mathematical operations, event-specific operations, and processed signals. The user parameter data 244 includes at least a cadence, a distance, a speed, a number of steps, a step time, a ground contact time, a number of strides, a stride length, a stride time, and ratios of these parameters. The number of steps is a count of the number of footsteps taken by the user. The step time is a duration of time between consecutive footsteps of the user. The step time is stored as a list of step times and/or an average step time. The ground contact time of the user is a duration of time that the user's foot is contact with the ground as the user performs bipedal movement, such as walking, running, or jogging, for example. The ground contact time is stored as a list of measured ground contact times and/or an average ground contact time. The number of strides is a count of the number of strides taken by the user. The stride length is a distance corresponding to a length of a stride taken by the user. The stride length is stored as a list of measured stride lengths and/or an average stride length. The stride time is a duration of time corresponding to each stride taken by the user. The stride time is stored as a list of stride times and/or an average stride time. The speed corresponds to the ground speed of the user. The speed is stored as a list of instantaneous speeds and/or an average speed. The distance corresponds to a distance traversed by the user. The cadence corresponds to the number of strides taken per time period of the user and/or the number of steps taken per time period by the user. For example, cadence is determined in steps per minute or strides per minute. Cadence may also be determined as an instantaneous cadence and/or an average cadence.

Additional user parameters may also be stored as the user parameter data 244 that are based on demographic data 242 (FIG. 7) and/or based on ratios of the aforementioned user parameters. For example, ratios of ground contact time/stride time, stride length/height of the user, and step length/height may be stored as the user parameter data 244. Moreover, variables such as peak acceleration and RMS acceleration may be also calculated from the acceleration data 188 and stored as the user parameter data 244 and/or movement data 136.

The battery 184 is configured to supply the movement sensor 170, the transceiver 174, the memory 178, and the controller 182 with electrical energy. In one embodiment, the battery 184 is a button cell battery or a coin cell battery that is permanently embedded in the housing 138 of the monitoring device 104, such that the battery 184 is not user accessible and cannot be replaced or recharged without destroying the monitoring device 104. Accordingly, the battery 184 stores a finite amount of electrical energy that cannot be replenished by the user. When the supply of electrical energy stored in the battery 184 is exhausted, the monitoring device 104 ceases to operate. In another embodiment, the battery 184 is a user-accessible rechargeable battery, such as a lithium polymer battery, that is configured to be recharged and/or replaced by the user.

The Shoe

Figure 3:
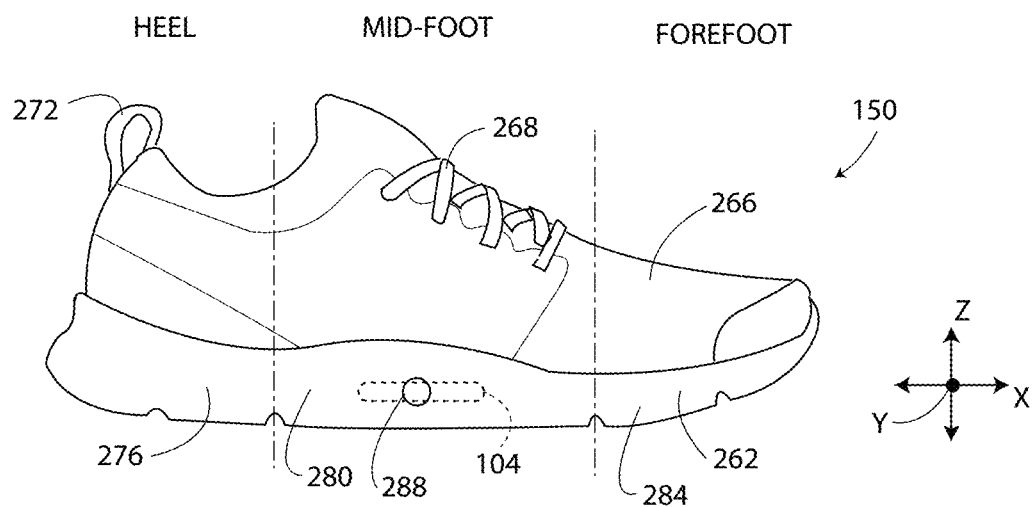
FIG. 3 is a side elevational view of an embodiment of a shoe including the monitoring device of FIG. 1.
Figure 4:
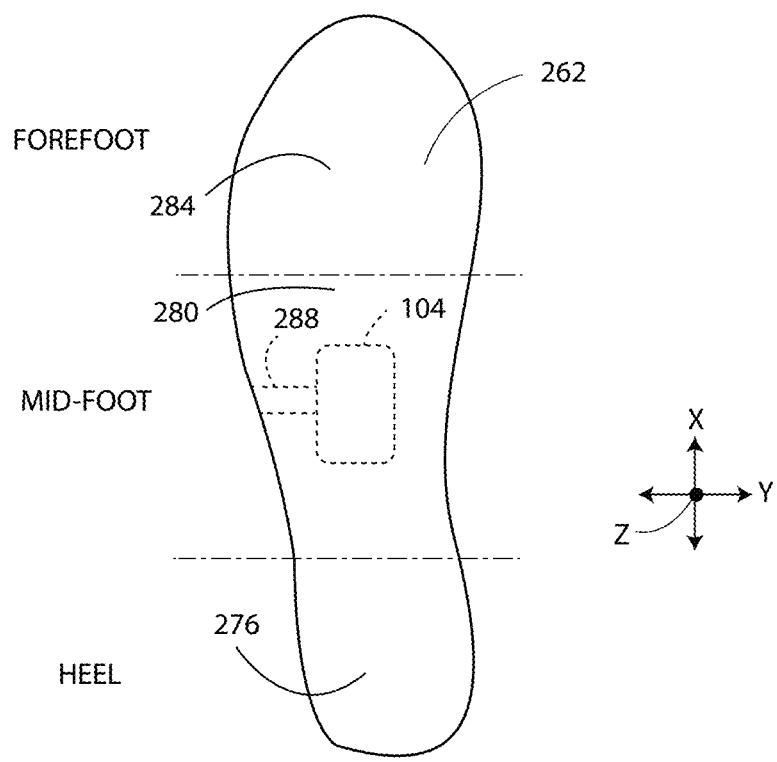
FIG. 4 is a bottom plan view of the shoe and the monitoring device of FIG. 3.

The monitoring device 104 is configured to be worn or carried by a user of the fitness tracking system 100. As shown in FIGS. 3 and 4, in one embodiment, the monitoring device 104 is mounted on or in a shoe 150 worn by the user. In at least some embodiments, the shoe 150 is included as an element of the fitness tracking system 100. The shoe 150 may include a sole portion 262 and an upper portion 266 extending from the sole portion 262. In some embodiments, laces 268 secure the shoe 150 to the user's foot and a pull loop 272 is provided at a rear of the upper portion 266 to assist the user in putting on the shoe 150.

The shoe 150 is shown relative to a set of reference axes including a horizontal X-axis that extends from the forefoot to the heel of the shoe 150, a horizontal Y-axis that is perpendicular to the X-axis and extends into and out of the page in FIG. 3, and a vertical Z-axis that is perpendicular to the X-axis and the Y-axis. On flat ground, the X-axis and the Y-axis are parallel to a plane defined by the ground and referred to herein as a ground plane.

The sole portion 262 of the shoe 150 includes three regions including a heel region 276, a midfoot region 280, and a forefoot region 284. The midfoot region 280 is located between the heel region 276 and the forefoot region 284. The dash-dot-dash boundary lines of the regions 276, 280, 284 as shown in FIGS. 3 and 4 are exemplary only and the position of the boundary lines may depend on the configuration of the sole portion 262 and the anatomy of the user's foot. For example, some sole portions 262 may have a wider heel region 276 and a narrower midfoot region 280. Whereas, other sole portions 262 may have a wider forefoot region 284, and a heel region 276 and midfoot region 280 of approximately equal lengths. Users typically select a shoe 150 having a sole portion 262 that is appropriate for their particular anatomy and running/walking dynamics.

The regions 276, 280, 284 of the sole portion 262 correspond to the foot strike patterns that are identifiable by the system 100. For example, if a portion of the heel region 276 is the first to contact the ground at the end of a user's stride, then the corresponding foot strike has a heel foot strike pattern. If a portion of the midfoot region 280 is the first to contact the ground at the end of a user's stride, then the corresponding foot strike has a midfoot foot strike pattern. If a portion of the forefoot region 284 is the first to contact the ground at the end of a user's stride, then the corresponding foot strike has a forefoot foot strike pattern.

As shown in FIGS. 3 and 4, the monitoring device 104 is located within the sole portion 262 of the shoe 150. Specifically, the monitoring device 104 is permanently affixed and/or permanently mounted to the shoe 150 within the sole portion 262, such that the monitoring device 104 cannot be removed from the shoe 150 without destroying the shoe 150. The monitoring device 104 may also be characterized as being permanently embedded within the sole portion 262 of the shoe 150. In the illustrated example, the housing 138 of the monitoring device 104 is fixed in position relative to the sole portion 262 at the midfoot region 280. The housing 138 is spaced apart from the bottom of the sole portion 262, such that no portion of the monitoring device 104 contacts the ground as the user walks or runs. Moreover, the monitoring device 104 does not press against the bottom of the user's foot during movement of the user.

In other embodiments, the monitoring device 104 is located within the sole portion 262 at any desired point along the X-axis from the rear most portion of the heel region 276 to the front most portion of the forefoot region 248. The monitoring device 104 may be located within two or more of the regions 276, 280, 284. For example, the monitoring device 104 may be located in the heel region 276 and the midfoot region 280, or the monitoring device 104 may be located in the midfoot region 280 and the forefoot region 284. Additionally, the monitoring device 104 may extend into all three regions 276, 280, 284 of the sole portion 262.

As shown in FIGS. 3 and 4, the sole portion 262 defines a window opening 288 to the monitoring device 104. The exemplary window opening 288 is a tubular cavity in the sole portion 262. In one embodiment, the window opening 262 extends towards the monitoring device 104, but does not extend to the monitoring device 104, such that the monitoring device 104 is not exposed to the atmosphere by the window opening 288. In another embodiment, the window opening 288 extends to the monitoring device 104 and exposes the housing 138 of the monitoring device 104 to the atmosphere. The window opening 288 is typically located at or near the transceiver 174, such that the window opening 288 is configured to reduce the power requirements for sending and receiving electronic signals with the transceiver 174. That is, the window opening 288 reduces the amount by which the sole portion 262 attenuates electromagnetic signals sent and received by the transceiver 174 of the monitoring device 104. The window opening 288 may also be configured as a waveguide configured to guide electromagnetic signals to and from the transceiver 174.

In the embodiment of the fitness tracking system 100 described above, the fitness tracking system 100 includes only one monitoring device 104 mounted to the one shoe 150. For example, the fitness tracking system 100 includes only one monitoring device 104 mounted on the user's right shoe 150. Thus, the fitness tracking system 100 is configured to determine foot strike characteristic data 200 for only the one shoe 150 and/or foot to which the monitoring device 104 is mounted. In this embodiment, the fitness tracking system 100 operates with the assumption that the user moves symmetrically and that the "unmonitored" foot and shoe have the same foot strike pattern as the "monitored" foot and shoe.

Other embodiments of the fitness tracking system 100 directly monitor the foot strike pattern for each foot and/or each shoe. Accordingly, in some embodiments, the fitness tracking system 100 includes two monitoring devices 104 each located in a corresponding shoe 150. That is, the system 100 includes a left shoe 150 having a left monitoring device 104 mounted thereon, and a right shoe 150 including a right monitoring device 104 mounted thereon. Both the left and the right monitoring devices 104 are configured for communication with the personal electronic device 108.

Figure 5:
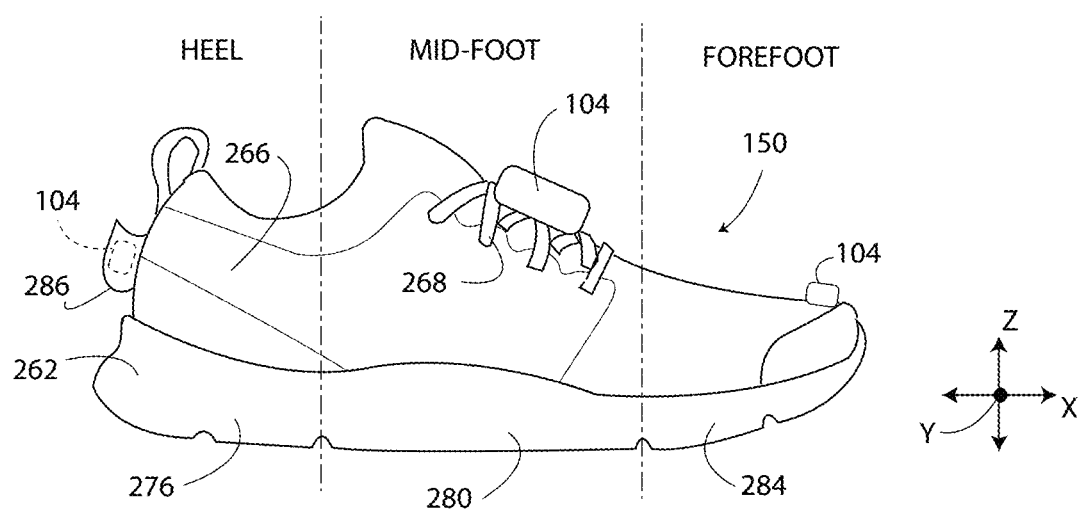
FIG. 5 is a side elevational view of another embodiment of a shoe including the monitoring device of FIG. 1.

As shown in FIG. 5, in other embodiments of the fitness tracking system 100, the monitoring device 104 is not permanently affixed to the shoe 150 and is instead removably mounted on the shoe 150. The monitoring device 104 of FIG. 5 is shown in three exemplary locations and other mounting locations are also possible. In the first exemplary mounting location, the monitoring device 104 is located in a pocket 286 of the heel region 276 of the shoe 150. In the second exemplary mounting location, the monitoring device 104 is attached to the laces 268. In the third exemplary mounting location, the monitoring device 104 is attached to the shoe 150 in the forefoot region 284. In each exemplary location, the monitoring device 104 is mounted securely to the shoe 150, such that the monitoring device 104 does not move relative to the shoe 150 during motion of the user. In this way, the monitoring device 104 generates acceleration data 188 that is an accurate representation of the acceleration of the user's foot as the user moves. The removably mounted monitoring device 104 enables the user to position the monitoring device 104 at a selected position along the X-axis that results in the highest accuracy of the foot strike characteristic data 200.

Figure 6:
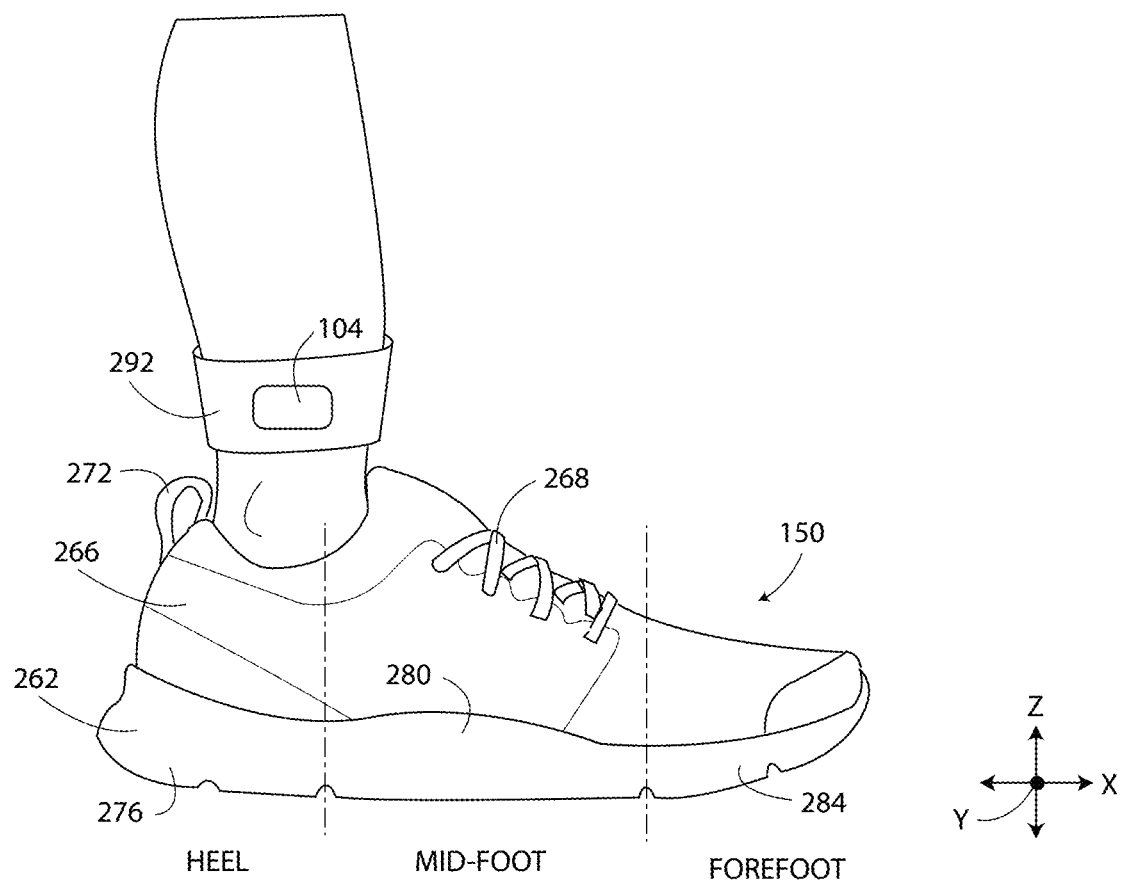
FIG. 6 is a side elevation view of a user's leg portion and a further embodiment of a shoe including the monitoring device of FIG. 1.

With reference to FIG. 6, in yet another embodiment, the monitoring device 104 is mounted on a strap 292. The strap 292 is configured to secure the monitoring device 104 to the leg of the user near the ankle (for example), such that the strap 292 and the monitoring device 104 are prevented from moving relative to the leg and the shoe 150 as the user moves. In this way, the monitoring device 104 generates acceleration data 188 that is an accurate representation of the acceleration of the user's foot as the user moves.

Unlike the embodiment shown in FIGS. 3 and 4, the monitoring devices 104 of FIGS. 5 and 6 can be used with any corresponding shoe or with the user wearing no shoes at all (i.e. barefoot). That is, the user is not required to wear shoes in order for the system 100 including the monitoring device 104 shown in FIG. 6 to generate the foot strike characteristic data 200.

The Personal Electronic Device

Figure 7:
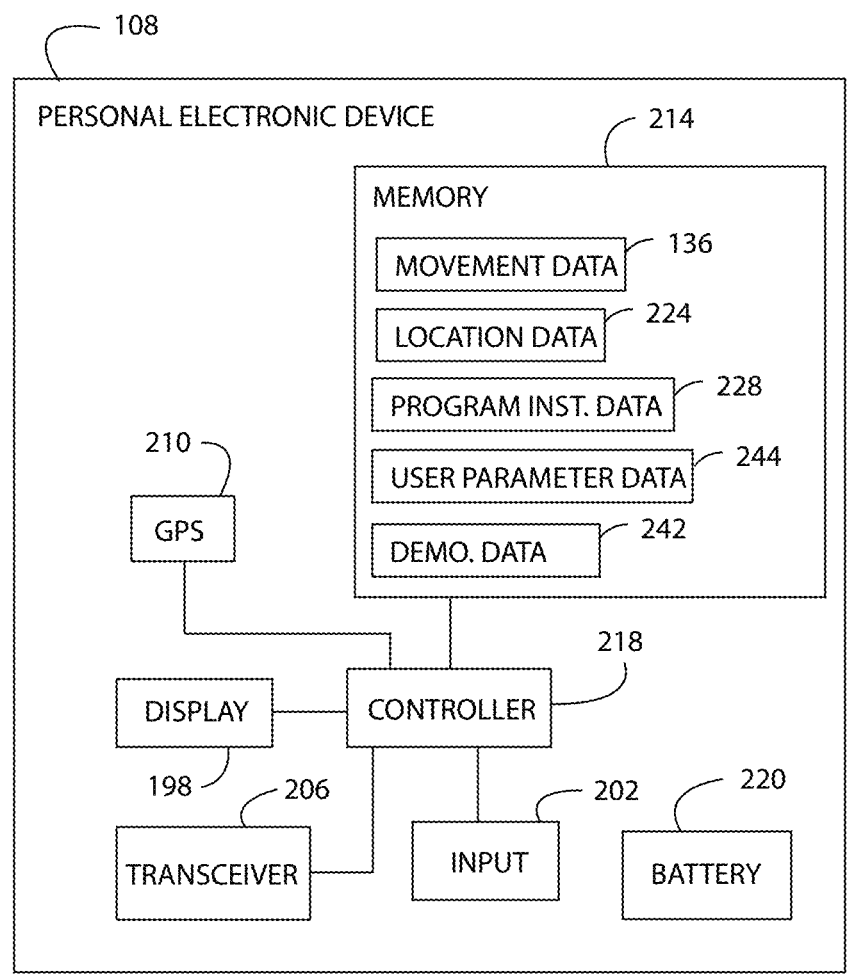
FIG. 7 is a block diagram of the personal electronic device of the fitness tracking system shown in FIG. 1.

As shown in FIG. 7, the personal electronic device 108 is configured as a smartphone. The personal electronic device 108 is configured for wireless communication with the monitoring device 104 and the remote processing server 112. In other embodiments, the personal electronic device 108 is provided as a smartwatch, an electronic wristband, or the like.

The personal electronic device 108 includes a display unit 198, an input unit 202, a transceiver 206, a GPS receiver 210, and a memory 214 each of which is operably connected to a controller 218 and a battery 220. The display unit 198 is configured as a liquid crystal display (LCD) panel configured to display static and dynamic text, images, and other visually comprehensible data based on at least the movement data 136 and the user parameter data 244. For example, the display unit 198 is configurable to display one or more interactive interfaces or display screens including, but not limited to, the foot strike pattern of the user, the foot strike characteristic data 200, a distance traversed by the user, a speed of the user, and a stride length of the user. The display unit 198, in another embodiment, is any display unit as desired by those of ordinary skill in the art.

The input unit 202 of the personal electronic device 108 is configured to receive input data from a user. The input unit 202 may be configured as a touchscreen applied to the display unit 198 that is configured to enable a user to supply input data via the touch of a finger and/or a stylus. In another embodiment, the input unit 202 comprises any device configured to receive input data, as may be utilized by those of ordinary skill in the art, including, for example, one or more buttons, switches, keys, microphones, cameras, and/or the like.

With continued reference to FIG. 7, the transceiver 206 of the personal electronic device 108 is configured to communicate wirelessly with the transceiver 174 of the monitoring device 104 and the remote processing server 112. The transceiver 206 wirelessly communicates with the remote processing server 112 either directly or indirectly via the cellular network 128 (FIG. 1), a wireless local area network ("Wi-Fi"), a personal area network, and/or any other wireless network over the Internet 124 (FIG. 1). Accordingly, the transceiver 206 is compatible with any desired wireless communication standard or protocol including, but not limited to, Near Field Communication ("NFC"), IEEE 802.11, Bluetooth®, Global System for Mobiles ("GSM"), and Code Division Multiple Access ("CDMA"). The transceiver 206 is configured to wirelessly transmit and receive data from the remote processing server 112, and to wirelessly transmit and receive data from the monitoring device 104.

The GPS receiver 210 of the personal electronic device 108 is configured to receive GPS signals from the GPS 132 (FIG. 1). The GPS receiver 210 is further configured to generate location data 224 that is representative of a current location on Earth of the personal electronic device 108 based on the received GPS signals. The location data 224, in one embodiment, includes latitude and longitude information. The controller 218 is configured to store the location data 224 generated by the GPS receiver 210 in the memory 214. The location data 224 may be synchronized with the foot strike characteristic data 200, so that the user can determine in which location(s) a certain foot strike pattern occurred.

As shown in FIG. 7, the memory 214 of the personal electronic device 108 is an electronic data storage unit, which is also referred to herein as a non-transient computer readable medium. The memory 214 is configured to store electronic data associated with operating the personal electronic device 108 and the monitoring device 104 including all or a subset of the movement data 136, the location data 224, program instruction data 228 including computer executable instructions for operating the personal electronic device, demographic data 242, and the user parameter data 244.

The demographic data 242 stored in the memory 214 is based on demographic information of the user and may include gender, height, weight, body mass index ("BMI"), and age, among other data. Any other user demographic, profile, and/or psychographic data may be included in the demographic data 242. Typically, the user supplies the personal electronic device 108 with the information that is stored as the demographic data 242.

The controller 218 of the personal electronic device 108 is configured to execute the program instruction data 228 in order to control the display unit 198, the input unit 202, the transceiver 206, the GPS receiver 210, and the memory 214. The controller 218 is configured to determine and/or to calculate the user parameter data 244 by applying, for example, the set of rules to the movement data 136. Depending on the embodiment, the controller 218 of the personal electrical device 108 may be configured to determine the movement data 136 including the foot strike characteristic data 200. The controller 218 is provided as a microprocessor, a processor, or any other type of electronic control chip.

The battery 220 is configured to supply the display unit 198, the input unit 202, the transceiver 206, the GPS 210, the memory 214, and the controller 218 with electrical energy. In one embodiment, the battery 220 a rechargeable lithium polymer battery that is configured to be recharged by the user.

The Remote Processing Server

As shown in FIG. 1, the remote processing server 112 is remotely located from the monitoring device 104 and the personal electronic device 108. The server 112 is located at a server physical location and the personal electric device 108 and the monitoring device 104 are located at one or more other physical locations that are different from the server physical location.

The server 112 includes a transceiver 252 and a memory 256 storing at least a portion of the movement data 136, program instructions 260, and at least a portion of the user parameter data 244. Each of the transceiver 252 and the memory 256 is operably connected to a central processing unit ("CPU") 264.

The transceiver 252 of the remote processing server 112 is configured to communicate wirelessly with the personal electronic device 108 either directly or indirectly via the cellular network 128, a wireless local area network ("Wi-Fi"), a personal area network, and/or any other wireless network. Accordingly, the transceiver 252 is compatible with any desired wireless communication standard or protocol including, but not limited to, Near Field Communication ("NFC"), IEEE 802.11, Bluetooth®, Global System for Mobiles ("GSM"), and Code Division Multiple Access ("CDMA").

The CPU 264 of the remote processing server 112 is configured to execute the program instruction data 260 to determine and/or to calculate at least one of the movement data and the user parameter data 244. The CPU 264 is configured to determine the user parameter data 244 by applying, for example, the set of rules to the movement data 136. Moreover, depending on the embodiment, the CPU 264 may be configured to determine the movement data 136 including the foot strike characteristic data 200.

The CPU 264 is provided as a microprocessor, a processor, or any other type of electronic control chip. Typically, the CPU 264 is more powerful than the controller 218 of the personal electronic device 108 and the controller 182 of the monitoring device 104, thereby enabling the remote processing server 112 to generate the movement data 136 and the user parameter data 244 more quickly than the devices 104, 108. In some embodiments of the fitness tracking system 100 the remote processing server 112 is not included and/or is not used.

Based on the above, any one or more of the monitoring device 104, the personal electronic device 108, and the remote processing server 112 is configured to determine the movement data 136 and the user parameter data 244. Moreover, the fitness tracking system 100 may selectively configure the monitoring device 104, the personal electronic device 108, and the remote processing server 112 to determine the movement data 136 and the user parameter data 244. For example, if the user is carrying only the monitoring device 104 and the personal electronic device 108 is separated from the user and outside of the communication range of the transceiver 174, then the fitness tracking system 100 may configure the monitoring device 104 to determine the movement data 136 and the user parameter data 244. In another example, if the user is carrying the monitoring device 104 and the personal electric device 108, but the personal electronic device 108 is out of communication range of the cellular network 128, then fitness tracking system 100 may configure the personal electronic device 108 to determine the movement data 136 and the user parameter data 244. In a further example, if the user is running with the monitoring device 104 and the personal electric device 108, and the personal electronic device 108 is within communication range of the cellular network 128, then fitness tracking system 100 may configure the remote processing server 112 to determine the movement data 136 and the user parameter data 244. Typically, the fitness tracking system 100 selects the configuration that results in an optimal use of resources for determining the movement data 136 and the user parameter data 244. In particular, the fitness tracking system 100 is configured to minimize power consumption of the monitoring device 104, while ensuring that the system 100 generates accurate movement data 136 and user parameter data 244.

Method of Operation

Figure 8:
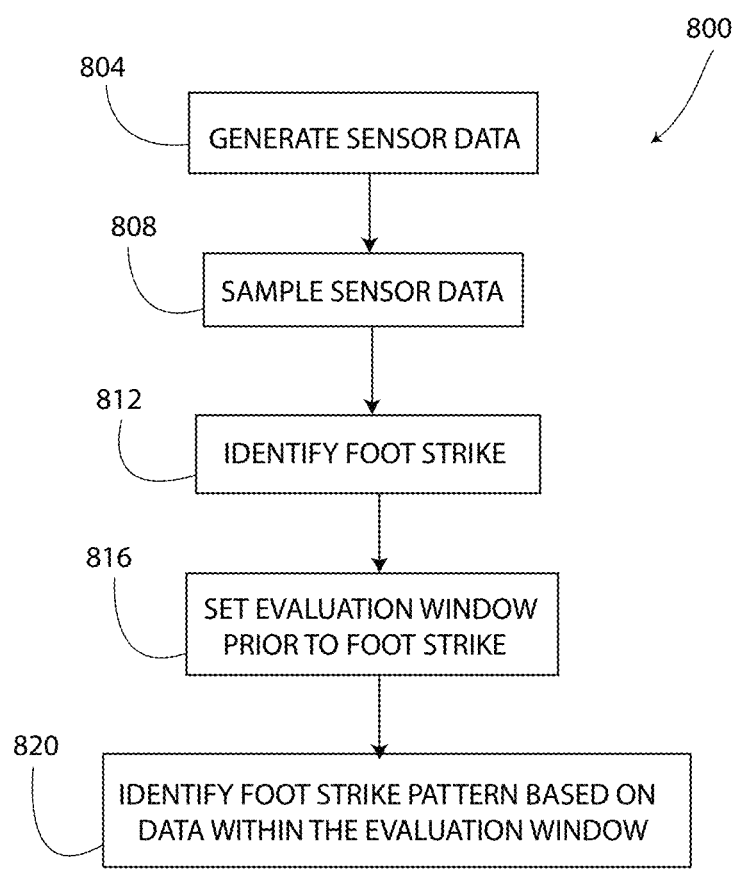
FIG. 8 is a flowchart illustrating an exemplary method of operating the fitness tracking system shown in FIG. 1.

As shown in the flowchart of FIG. 8, the fitness tracking system 100 is configured to execute a method 800 for determining the foot strike pattern of the user based on the acceleration data 188 generated by the movement sensor 170. Specifically, the method 800 includes determining the foot strike pattern based on the acceleration data 188 generated prior to the corresponding foot strike. Exemplary embodiments of the method 800 are set forth below.

In block 804, the method 800 includes generating the acceleration data 188 with the movement sensor 170 of the monitoring device 104. Typically, the user is walking, running, jogging, or otherwise moving, and the acceleration data 188 corresponds to acceleration of the user's foot (and the shoe 150) along a vertical axis, which is represented by the Z-axis in FIG. 3, for example.

Next, in block 808, at least one of the controller 182, the controller 218, and the CPU 264 samples the acceleration data 188 and stores the data as the sampled acceleration data 190. The acceleration data 188 is sampled at a sampling rate. The sampling rate, in one embodiment, ranges from 50 Hz to 2 kHz, depending on the embodiment. The sampled acceleration data 190 includes a plurality of acceleration data points that each include an acceleration value and a time value. The acceleration data 188 may be sampled raw, filtered, smoothed, or unsmoothed.

Figure 9:
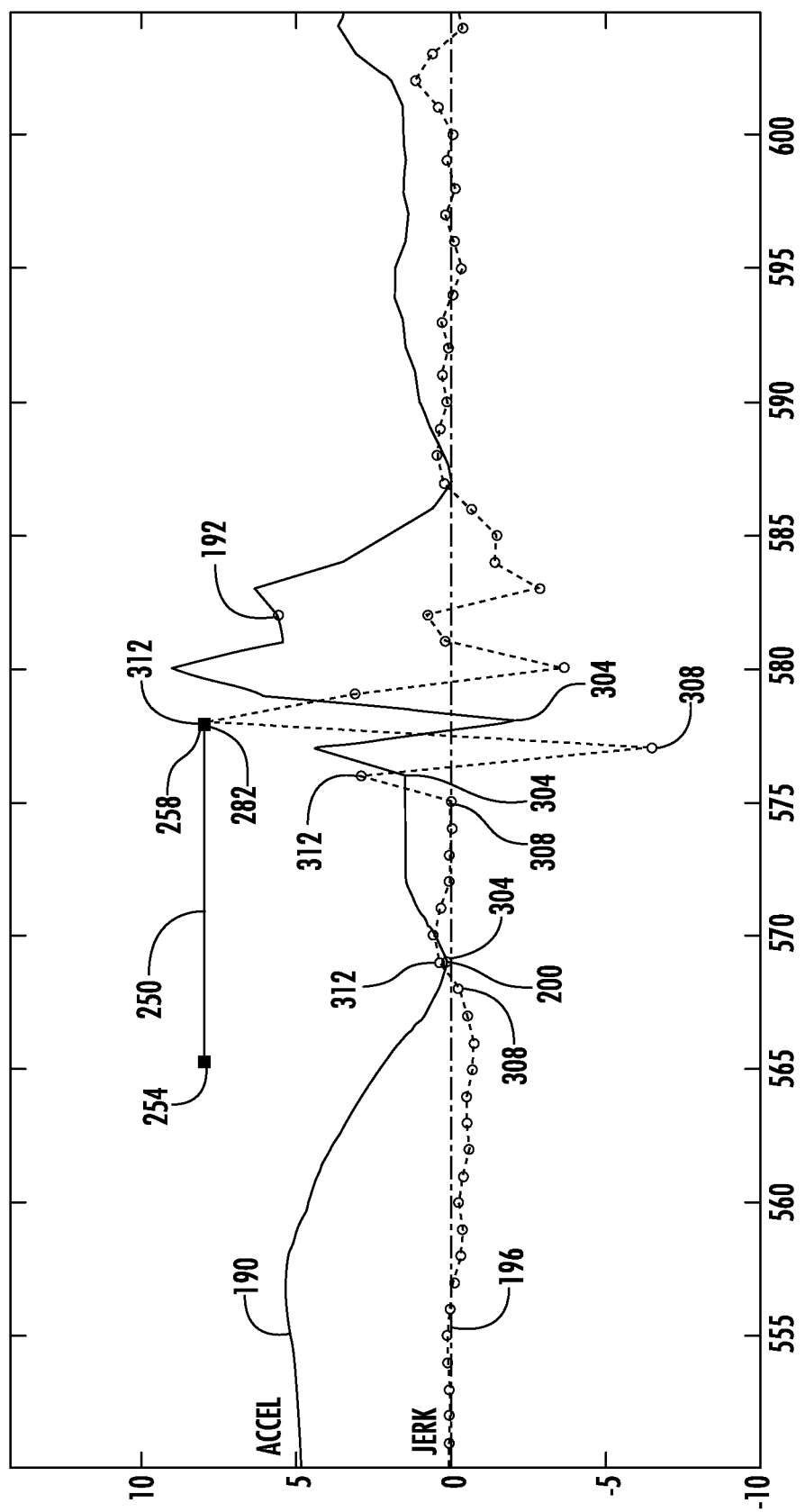
FIG. 9 is a graph of sampled acceleration data and jerk data generated by the fitness tracking system of FIG. 1.

With reference to block 812 and FIG. 9, next at least one of the controller 182, the controller 218, and the CPU 264 identifies the foot strike data 192. The "foot strike" occurs when the shoe 150 (or the user's foot) strikes the ground at the end of a stride. The foot strike data 192 corresponds to the acceleration of the user's foot or the shoe 150 during a foot strike. In FIG. 9, a data point of the foot strike data 192 is identified in a plot of the sampled acceleration data 190. FIG. 9 also plots the jerk value data 196, which is the numerical derivative of the sampled acceleration data 190. The "jerk" is also known as "jolt," "surge," and "lurch." The foot strike data 192 is a selected one of the data points of the sampled acceleration data 190.

The foot strike data 192 is determined according to any known approach. For example, the foot strike data 192 is determined by processing the sampled acceleration data 190 to determine when the acceleration passes a predetermined acceleration threshold. Additionally or alternatively, the foot strike data 192 is determined by processing the jerk value data 196 to determine when the jerk has passed a predetermined jerk threshold.

Next, according to block 816 and as shown in FIG. 9, the system 100 determines the location of an evaluation window 250 (i.e. an evaluation time window) having a start point 254 and an end point 258. The evaluation window 250 is a window of time and/or a window of data points in which a data point of the foot strike characteristic data 200 is located. As shown in FIG. 9, the evaluation window 250 is located prior in time to the foot strike data 192. That is, all of the data points included in the evaluation window 250 are prior to the foot strike data 192. The evaluation window 250 has a width corresponding to a predetermined number of data points that ranges from ten to fifty, for example. The predetermined number of data points included in the evaluation window 250 is based on at least one of the cadence of the user, the ground contact time of the user, the speed of the user, and the stride length of the user. Typically, the evaluation window 250 includes fewer data points in response to an increasing cadence, a decreasing ground contact time, an increasing speed, and an increasing stride length. The evaluation window 250 typically includes more data points in response to a decreasing cadence, an increasing ground contact time, a decreasing speed, and a decreasing strike length. Alternatively, the width of the evaluation window 250 is based on any other factor including any other parameter of the movement data 136, the user parameter data 244, and the demographic data 242. Further still, the evaluation window 250 may have a constant width that is unchanged by the system 100.

In an exemplary embodiment, the location of the evaluation window 250 relative to the foot strike data 192 is based on the jerk value data. Specifically, with reference to FIG. 9, the system 100 identifies a maximum absolute value of jerk 282 (hereinafter the max jerk value) that occurs within a predetermined time period prior to the foot strike data 192. The max jerk value 260 may be highly negative or highly positive. The system 100 locates the end point 258 of the evaluation window 250 at the max jerk value 260. The start point 254 of the evaluation window 250 is located the predetermined number of data points prior to the end point 258.

Next, with reference to block 820, the foot strike characteristic data 200 is identified within the evaluation window 250. To begin, the system 100 identifies each local minimum 304 of the sampled acceleration data 190 located within the evaluation window 250. If a different sign convention were to be used and the z-axis acceleration data 190 was flipped about the x-axis (i.e. the horizontal axis), then these local minima would instead be local maxima. For the purposes of this document, the reference to a "local minimum" will also refer to a "local maximum" for the condition where the acceleration data 190 is flipped. A local minimum 304, as used herein, occurs as the bottom of a trough of the sampled acceleration data 190 and has a pair of corresponding jerk values associated with it (a negative jerk value and a positive jerk value, which define the change from negative slope to positive slope in the acceleration data 190 and thus define a local minimum 304). In the exemplary data of FIG. 9, there are three local minima 304 of the sampled acceleration data 190 located within the evaluation window 250. Due to processing delays and the particular sampling rate of the data used to generate FIG. 9, the jerk value data 196 may be shifted slightly relative to the sampled acceleration data 190. The local minima 304 are identified by processing the jerk value data 196 to identify when jerk values change signs from negative values to positive values. In other embodiments, the local minima 304 are identified using any other suitable data processing technique.

For each identified local minima 304 in the evaluation window 250, the system 100 identifies a corresponding pair of jerk value data points including a negative jerk value 308 and a positive jerk value 312. These values 308, 312 are present for each local minima 304 based on the definition of a minimum and the definition of the jerk, which is the numerical derivative of the sampled acceleration data 190. The system 100 sums the absolute values of the corresponding pair of jerk value data points 308, 312 for each of the identified local minima 304 in the evaluation window 250. The system 100 identifies the foot strike characteristic data 200 as occurring at the local minimum 304 having the pair of jerk value data points 308, 312 resulting in the smallest sum of absolute values. In FIG. 9, the system 100 identifies the acceleration value at the leftmost local minimum 304 as the foot strike characteristic data 200 associated with the foot strike data 192.

In a numerical example, the pair of jerk value data points 308, 312 for the left local minimum 304 has a negative jerk value 308 having an absolute value of 0.5 and a positive jerk value 312 having an absolute value of about 0.5, resulting in a sum of 1.0. The pair of jerk value data points 308, 312 for the middle local minimum 304 has a negative jerk value 308 having an absolute value very close to 0.0 and a positive jerk value 312 having an absolute value of about 3.0, resulting in a sum of 3.0. The pair of jerk value data points 308, 312 for the right local minimum 304 has a negative jerk value 308 having an absolute value 6.5 and a positive jerk value 312 having an absolute value of about 8.0, resulting in a sum of 14.5. After determining the sums (i.e. 1.0, 3.0, and 14.5), the system 100 determines that the sum having the value of 1.0 is the smallest. Based on the above, the system 100 identifies the acceleration value at the left local minimum 304 as the acceleration value that corresponds to the foot strike characteristic data 200. In at least one embodiment, the algorithmic approach applied by the system 100 to the sampled acceleration data 190 and the jerk value data 196 located within the evaluation window 250 selects as the foot strike characteristic data 200 the acceleration value at the local minimum 304 of the sampled acceleration data 190 that has the most gradual transition from a negative slope to a positive slope.

In an alternative embodiment, instead of summing the absolute values of the pairs of jerk value data points 308, 312, the system 100 averages the absolute values. The average value is determined by summing the absolute values of the pairs of jerk value data points 308, 312 and dividing the sum by two. The system 100 identifies the foot strike characteristic data 200 as the acceleration value at the local minimum 304 corresponding to the smallest averaged value.

The system 100 applies one of at least two approaches for identifying the local minima 304 of the sampled acceleration data 190. In a first approach, the system 100 processes the data within the evaluation window 250 to identify the local minima 304 after the foot strike data 192 is identified. In a second approach, the system 100 continuously processes the sampled acceleration data 190 and the jerk value data 196 to identify local minima 304 and corresponding pairs of jerk value data 308, 312 without reference to an evaluation window 250. The identified local minima 304 and the corresponding pairs of jerk value data 308, 312 are stored in at least one of the memories 178, 214, 256. When a foot strike is detected, system 100 determines the location of the evaluation window 250 and then evaluates the stored local minima 304 within the evaluation window 250 to determine the acceleration value at the local minimum 304 that corresponds to the foot strike characteristic data 200.

In some instances, the system 100 may determine that there are no local minima 304 of the sampled acceleration data 190 located within the evaluation window 250. In this situation, the system 100 determines the foot strike characteristic data 200 as the point of the sampled acceleration data 190 having the smallest corresponding absolute value of jerk.

The system 100 determines the foot strike pattern of the user with sampled acceleration data 190 that was generated prior to the corresponding foot strike 192. In FIG. 9, the X-axis represents time and all of the data points of the evaluation window 250 represent acceleration or jerk of the movement sensor 170 that occurred before the user's foot or shoe 150 struck the ground. That is, the movement sensor 170 was suspended in air and shoe 150 was not in contact with the ground as the foot strike characteristic data 200 was generated by the system 100. Thus, the system 100 recognizes that the acceleration of the shoe 150 prior to the corresponding foot strike 192 offers determinative clues as to the type of foot strike that is about to occur. The system 100, in at least one embodiment, forecasts or predicts the foot strike pattern based on events (i.e. acceleration and jerk) occurring prior to the corresponding foot strike.

Figure 10:
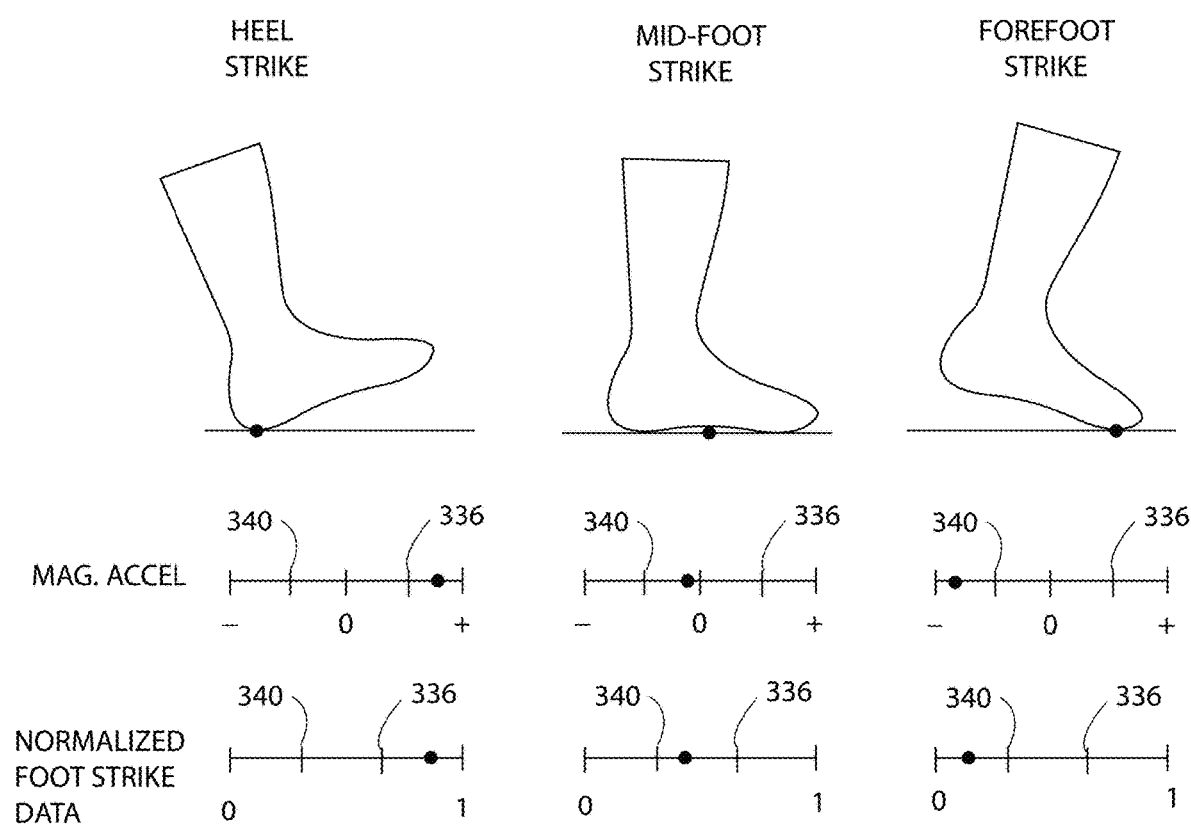
FIG. 10 is a diagram illustrating three exemplary foot strike patterns including the heel foot strike pattern, the midfoot foot strike pattern, and the forefoot foot strike pattern.

With reference to FIG. 10, the value of the foot strike characteristic data 200 is indicative of the foot strike pattern of the user. Specifically, if the acceleration value of the foot strike characteristic data 200 is greater than a first predetermined threshold 336, then the system 100 determines that the corresponding foot strike was a heel strike. If the acceleration value of the foot strike characteristic data 200 is less than a second predetermined 340 threshold, then the system 100 determines that the corresponding foot strike was a forefoot strike. If the acceleration value of the foot strike characteristic data 200 is less than or equal to the first predetermined threshold 336 and greater than or equal to the second predetermined threshold 340, then the system 100 determines that the corresponding foot strike was a midfoot foot strike pattern. The values of the first and second predetermined thresholds 336, 340 may be based on the user parameter data 244 and/or the demographic data 242.

In one embodiment, the system 100 normalizes the foot strike characteristic data 200 to have values ranging from only zero to one, for example. Accordingly, the foot strike characteristic data 200 represents a continuum of foot strike characteristics ranging from heel strike at one end of the range to forefoot strike at the opposite end of the range. In other embodiments, the foot strike characteristic data 200 is normalized to include values within any desired numerical range. Exemplary normalized data is shown in FIG. 10, along with an exemplary first predetermined threshold 336 located at about 0.66, and an exemplary second predetermined threshold located at about 0.33.

Figure 11:
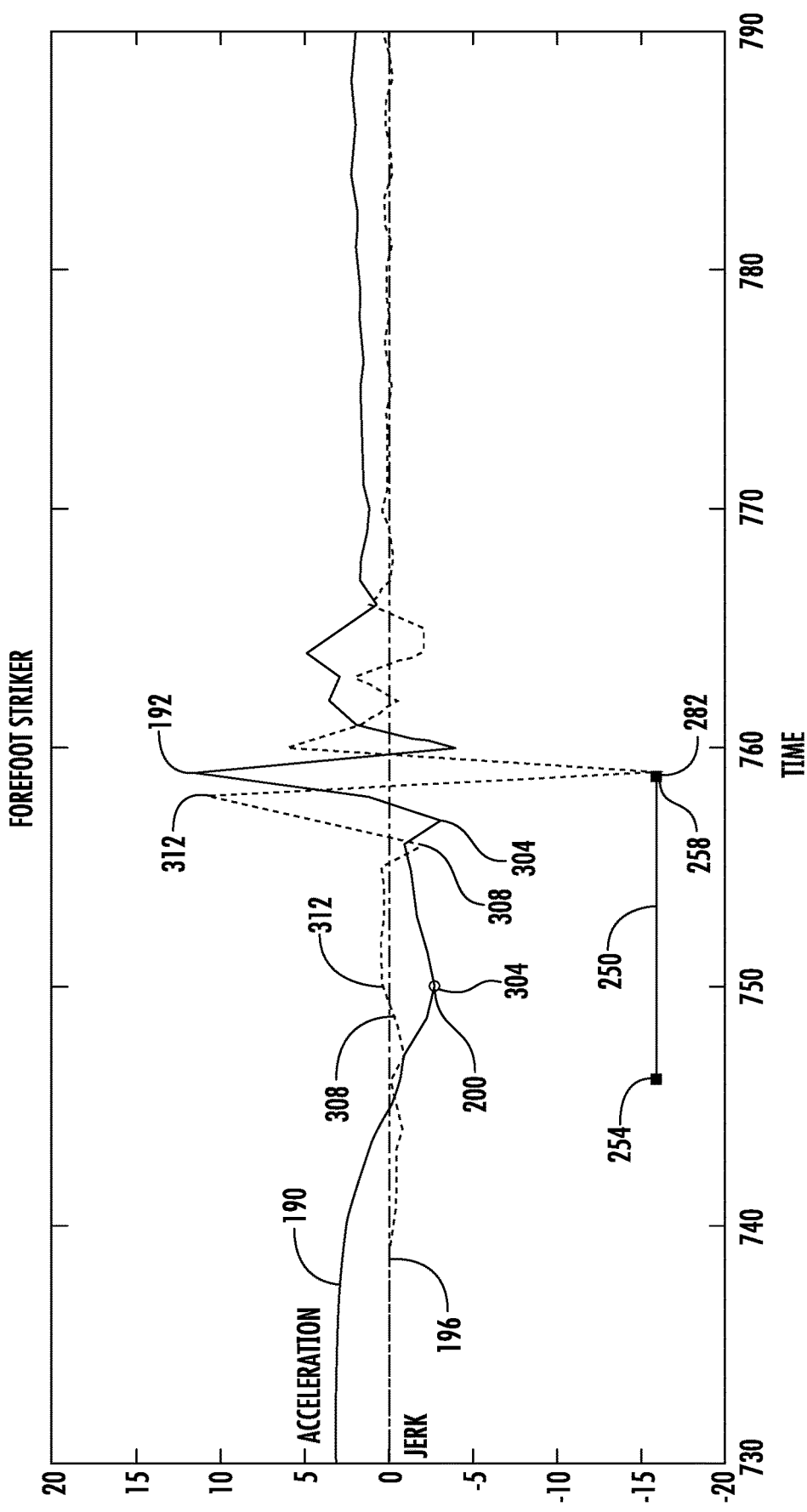
FIG. 11 is a graph of acceleration data and jerk data generated by the fitness tracking system of FIG. 1 and corresponding to the forefoot foot strike pattern.

As shown in FIG. 11, additional sampled acceleration data 190 and jerk value data 196 are plotted versus time. In FIG. 11, the foot strike data 192 is identified and the system 100 has determined the location of the evaluation window 250 based on the maximum absolute value of jerk 282. The system 100 has identified two local minima 304 within the evaluation window 250. The left local minimum 304 has the pair of jerk value data points 308, 312 with the smallest sum of absolute values and, thus, corresponds to the foot strike characteristic data 200. Moreover, since the value of the foot strike characteristic data 200 is negative and is less than the predetermined threshold 340, the foot strike data 192 tends to correspond to a forefoot foot strike pattern.

Figure 12:
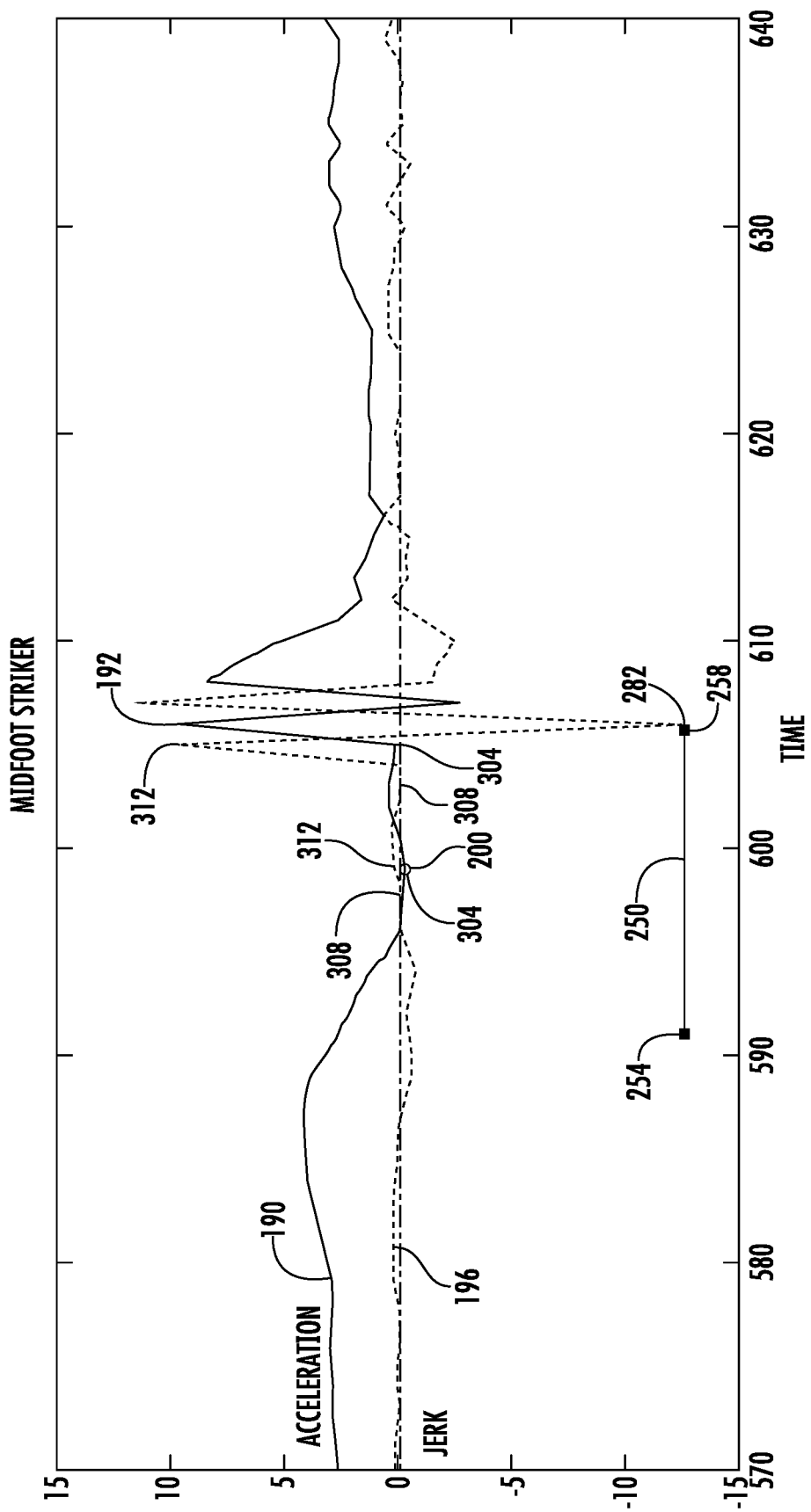
FIG. 12 is a graph of acceleration data and jerk data generated by the fitness tracking system of FIG. 1 and corresponding to the midfoot foot strike pattern.

In FIG. 12, further sampled acceleration data 190 and jerk value data 196 are plotted versus time. In FIG. 12, the foot strike data 192 is identified and the system 100 has determined the location of the evaluation window 250 based on the maximum absolute value of jerk 282. The system 100 has identified two local minima 304 within the evaluation window 250. The left local minimum 304 has the pair of jerk value data points 308, 312 with the smallest sum of absolute values. Moreover, since the value of the foot strike characteristic data 200 is near zero (i.e. greater than the predetermined threshold 340 and less than the predetermined threshold 336), the foot strike data 192 tends to correspond to a midfoot foot strike pattern.

Figure 13:
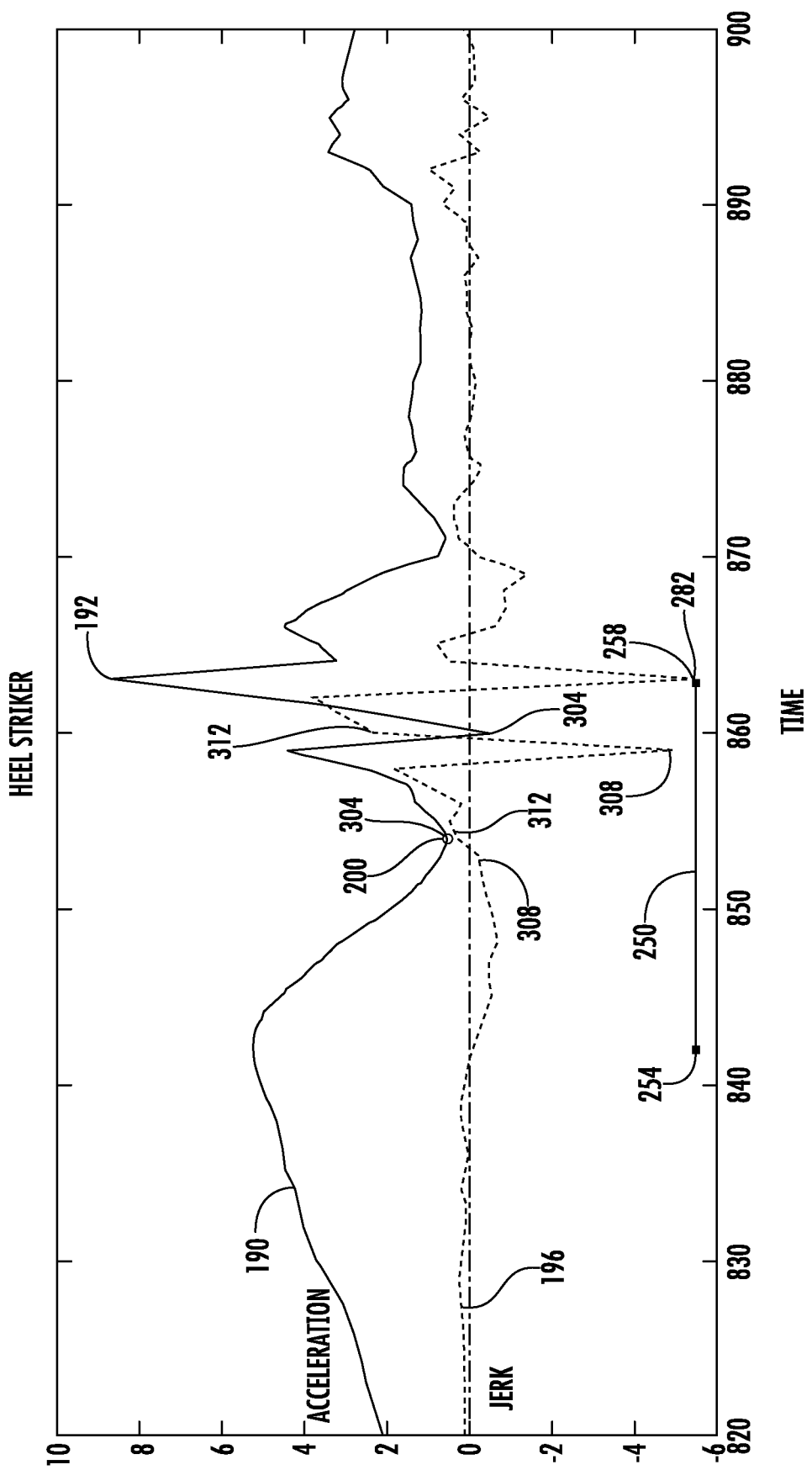
FIG. 13 is a graph of acceleration data and jerk data generated by the fitness tracking system of FIG. 1 and corresponding to the heel foot strike pattern.

In FIG. 13, additional sampled acceleration data 190 and jerk value data 196 are plotted versus time. In FIG. 13, the foot strike data 192 is identified and the system 100 has determined the location of the evaluation window 250 based on the maximum absolute value of jerk 282. The system 100 has identified two local minima 304 within the evaluation window 250. The left local minimum 304 has the pair of jerk value data points 308, 312 with the smallest sum of absolute values. Moreover, since the value of the foot strike characteristic data 200 is positive and is greater than the predetermined threshold 336, the foot strike data 192 tends to correspond to a heel foot strike pattern.

The system 100 determines the foot strike characteristic data 200 for each detected foot strike 192 of the user that occurs during a workout, for example, and stores the foot strike characteristic data 200 in at least one of the memories 178, 214, 256. The personal electronic device 108 is configured to display data based on the foot strike characteristic data 200 to the user on the display unit 198 during the workout and/or after the workout. For example, following a workout, the system 100 may display the foot strike characteristic data 200 to the user as a classification result. That is, the system 100 identifies the user as exhibiting only one of the heel foot strike pattern, the midfoot foot strike pattern, or the forefoot foot strike pattern. Additionally or alternatively, the system 100 displays a single value to the user that is representative of the user's foot strike pattern. For example, in addition to identifying the user as having a heel foot strike pattern, the system may display the number "0.95" to indicate that on a normalized scale of zero corresponding to a forefoot strike pattern and one corresponding to a heel foot strike pattern, the user has a predominant heel foot strike pattern. Additionally or alternatively, the system 100 may display a confidence interval so that the user is able to gauge the accuracy of the foot strike characteristic data 200. For example, the system may display the number "0.90±0.05" to indicate that the user has a predominant heel strike pattern and that there is little uncertainty about that assessment. Alternatively, the user may be provided with a confidence score within a range of 0% to 100% confidence.

In a further example, some users, including trail runners for example, are expected to exhibit a range of foot strike patterns during a workout depending on the type of terrain on which the user is running. Accordingly, the system 100 may be configured to display to the user the percentage of foot strikes falling into each of the three main categories. For example, after a trail run the system 100 may display that 15% of the detected foot strikes exhibited the heel foot strike pattern, 60% of the detected foot strikes exhibited the midfoot foot strike pattern, and 25% of the detected foot strikes exhibited the forefoot foot strike pattern.

Moreover, in some embodiments, the system 100 displays a change in the foot strike pattern of the user over time. For example, the system 100 may store foot strike characteristic data 200 of the user for multiple workouts. The system 100 may identify the user as having a midfoot foot strike pattern for five workouts in a row. Following a sixth workout, however, the system 100 identifies the user as having a heel foot strike pattern. The system 100 displays an alert or notification to the user (using the display unit 198, for example) regarding the detected change in foot strike pattern so that the user can take corrective actions, if necessary. Corrective actions include replacing the user's shoes, reducing user fatigue prior to workouts, and seeking medical attention. In another example, the user is engaged in an hour long run. During the first 45 minutes, the system 100 determines that the user exhibits the midfoot foot strike pattern. During minutes 45 to 50, however, the system 100 determines that the user has changed to the heel foot strike pattern. The system 100 displays an alert or notification to the user regarding the change in foot strike pattern so that the user can take corrective actions, if necessary. Corrective actions include reducing fatigue, rehydrating, adjusting the laces 268, and running with greater focus on proper form.

In some embodiments, the fitness tracking system 100 uses the foot strike characteristic data 200 to improve accuracy in the determination of the user parameter data 244. For example, the system 100 may determine the stride length of the user more accurately when the foot strike pattern of the user is taken into account.

Advantages of the Fitness Tracking System

The fitness tracking system 100 is an improved computer that generates accurate data for the user and conserves electrical power while doing so. For example, in one embodiment, the system 100 generates the foot strike characteristic data 200 using the acceleration data 188 from only a single axis of movement (typically the vertical axis). As a result, the electrical power demands of the monitoring device 104 are drastically reduced as compared to prior art devices that are required to generate foot strike pattern data using sensor data from multiple axes of movement. Less electrical energy is consumed to generate the single-axis-based foot strike characteristic data 200 as compared to the multi-axis based prior art foot strike pattern data. Since, in some embodiments, the battery 184 of the monitoring device 104 cannot be replaced or recharged, and the method 800 is a means of increasing the service of life of the monitoring device 104 and improving the operation thereof. Moreover, the method 800 of operating the fitness tracking system 100 cannot be performed in the mind of a person.

In another embodiment, the components and functionality of the personal electronic device 108 are included in the monitoring device 104. In such an embodiment, the fitness tracking system 100 does not include the personal electronic device 108 and the monitoring device 104 is configured to communicate directly with the remote processing server. 112.

In a further embodiment, the fitness tracking system 100 does not include the personal electronic device 108 and the remote processing server 112, and includes only the monitoring device 104. In such an embodiment, the monitoring device 104 includes all of the components and hardware for performing the method 800 of FIG. 8. In such an embodiment, the monitoring device 104 is configured to transmit the movement data 136 and/or the user parameter data 244 to an external device for viewing by the user.

Method of Estimating Movement Efficiency

Figure 14:
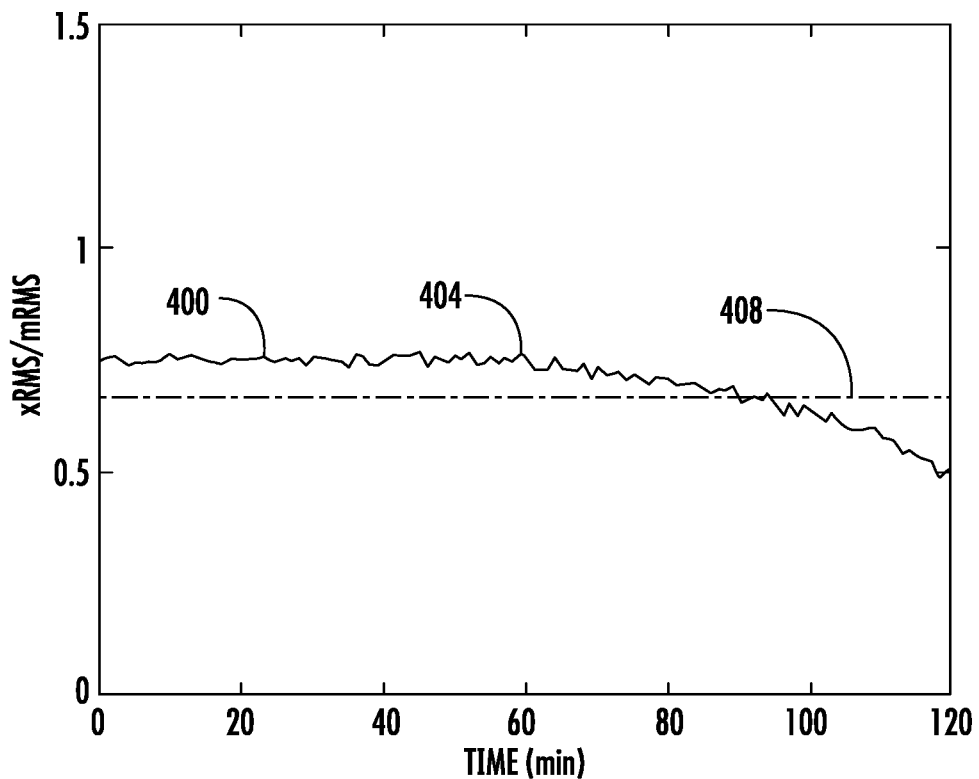
FIG. 14 is a graph of a movement efficiency variable versus time.
Figure 15:
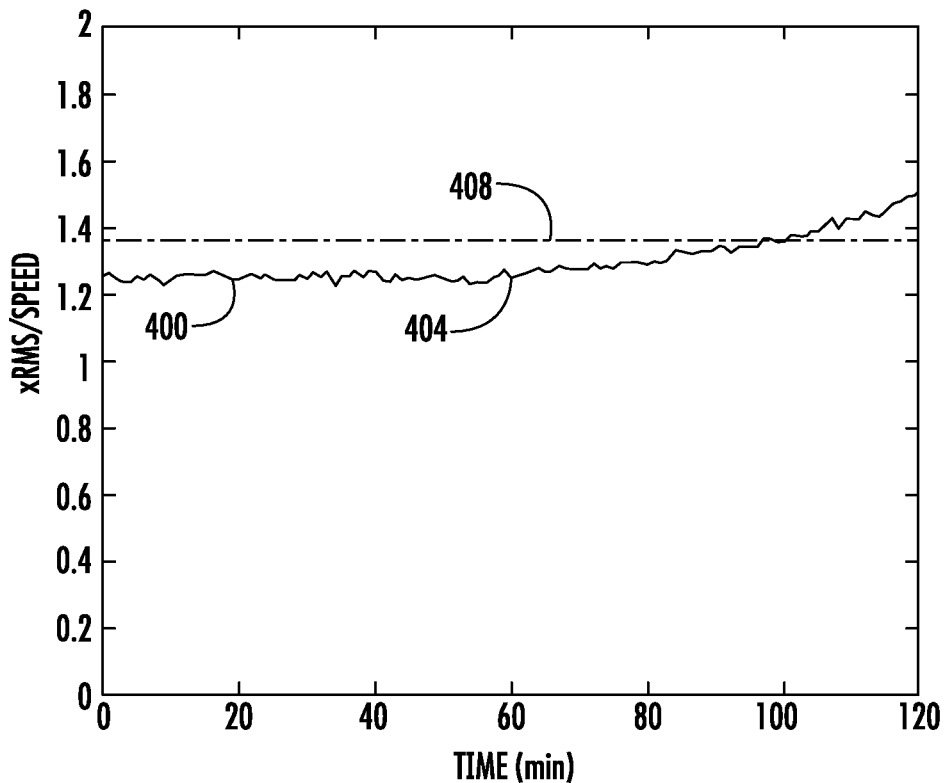
FIG. 15 is another graph of the movement efficiency variable versus time.

As shown in FIGS. 14 and 15, the system 100, as disclosed herein, is also configured to estimate a movement efficiency variable 400 of the user. The movement efficiency of the user corresponds to a level of fatigue of the user. In the embodiment of FIG. 14, a high value of the movement efficiency variable 400 corresponds to low levels of user fatigue as may be experienced by the user at the beginning of a workout, and a low value of the movement efficiency variable 400 corresponds to high levels of user fatigue as may be experienced by the user during the workout or at the end of the workout. Whereas, in the embodiment of FIG. 15, a low value of the movement efficiency variable 400 corresponds to low levels of user fatigue as may be experienced by the user at the beginning of a workout, and a high value of the movement efficiency variable 400 corresponds to high levels of user fatigue as may be experienced by the user during the workout or at the end of the workout.

The system 100 determines the movement efficiency variable 400 based on the data generated by the movement sensor 170. Any one or more of the monitoring device 104, the personal electronic device 108, and the remote processing server 112 may be configured to calculate the movement efficiency variable 400.

As previously mentioned, the foot strike characteristic data can be used as a metric to help assess fatigue status. Therefore, in some embodiments, the movement efficiency variable 400 can be derived from the foot strike characteristic data. Other methods are also possible for calculating the movement efficiency variable 400 though. With reference to FIG. 14, in one embodiment, the system 100 calculates the movement efficiency variable 400 as a ratio of a root mean square ("RMS") of an X-axis acceleration to an RMS of the acceleration magnitude. The X-axis acceleration corresponds to the acceleration of the shoe 150 along the X-axis as shown in FIG. 3, for example. The RMS of the acceleration magnitude is the RMS of a magnitude of a combined acceleration (i.e. a resultant acceleration, for example) of a multi-axis accelerometer. For example, the combined acceleration combines at least two of an X-axis acceleration magnitude, a Y-axis acceleration magnitude, and a Z-axis acceleration magnitude into a single acceleration magnitude value.

As shown in FIG. 14, an onset of fatigue 404 is identified in the movement efficiency variable 400 at about the sixty minute mark. The onset of fatigue 404 is a point during the workout that the movement efficiency of the user begins to trend toward a predetermined fatigue level 408. Prior to reaching the predetermined fatigue level 408, the user's movement efficiency is suitable for active training with proper form. Whereas, subsequent to the predetermined fatigue level 408, the user's movement efficiency tends to be unsuitable for active training with proper form and the user tends to be working out with an increased risk of injury. Changes in the movement efficiency variable 400 over time are correlated to the onset of fatigue 404.

Any one or more of the controller 182, the controller 218, and CPU 264 may be configured to calculate the movement efficiency variable 400 and the onset of fatigue 404. In one embodiment, the system 100 applies a dimensionality reduction method, such as principal component analysis (PCA), to at least the sampled acceleration data 190 to determine the movement efficiency variable 400.

The system 100 is configured to display a fatigue status to the user based on at least one of the movement efficiency variable 400 and the onset of fatigue 404. The fatigue status may be displayed (on the display unit 198 of the personal electronic device 108, for example) as a summary metric or as a time series. The summary metric may correspond to a single "fatigue number" that is representative of the user's level of fatigue as detected by the system 100. For example, the fatigue number may be a number within a normalized range of zero to one hundred, with zero corresponding to low levels of fatigue and one hundred corresponding to high levels of fatigue. The time series may correspond to a display of multiple values of the fatigue status corresponding to various time points of a workout monitored by the system 100.

As shown in FIG. 15, in another embodiment, the system 100 calculates the movement efficiency variable 400 as a ratio of the RMS of the acceleration magnitude to the speed of the user as determined by the system 100. The speed of the user may be determined based on the movement data 136 and the user parameter data 244 and/or using the GPS 132 and the GPS receiver 210 of the personal electronic device 108.

In other embodiments, the system 100 calculates the movement efficiency variable 400 by analyzing all of a subset of the following variables: (i) RMS of the X-axis acceleration (xRMS), (ii) RMS of the Y-axis acceleration (yRMS), (iii) RMS of the Z-axis acceleration (zRMS), (iv) RMS of the acceleration magnitude (mRMS), (v) a ratio of xRMS/mRMS, (vi) a ratio of yRMS/mRMS, (vii) a ratio of zRMS/mRMS, (viii) xRMS divided by the speed of the user, (ix) yRMS divided by the speed of the user, (x) zRMS divided by the speed of the user, (xi) mRMS divided by the speed of the user, and (xii) foot strike characteristic data. A dimensionality reduction method, such as principal component analysis (PCA), may be applied to some or all of these variables to determine new variables that may be used to assess movement efficiency.

It will be appreciated that the various ones of the foregoing aspects of the present disclosure, or any parts or functions thereof, may be implemented using hardware, software, firmware, tangible, and non-transitory computer readable or computer usable storage media having instructions stored thereon, or a combination thereof, and may be implemented in one or more computer systems.

The above described system and method solves a technological problem common in industry practice related to analysis of collected activity data. Moreover, the above-described system and method improves the functioning of the computer device by verifying collected data against other data for that activity type, while also allowing the user to switch between activities while automatically determining the new activity type.

While the disclosure has been illustrated and described in detail in the drawings and foregoing description, the same should be considered as illustrative and not restrictive in character. It is understood that only the preferred embodiments have been presented and that all changes, modifications and further applications that come within the spirit of the disclosure are desired to be protected.

It will be apparent to those skilled in the art that various modifications and variations can be made in the disclosed embodiments of the disclosed device and associated methods without departing from the spirit or scope of the disclosure. Thus, it is intended that the present disclosure covers the modifications and variations of the embodiments disclosed above provided that the modifications and variations come within the scope of any claims and their equivalents.

What is claimed is:

1. A fitness tracking system comprising:
   a shoe;
   a monitoring device mounted on the shoe and including an accelerometer configured to generate acceleration data corresponding to acceleration of a foot received by the shoe; and
   a controller operably connected to the accelerometer, the controller configured to collect sampled acceleration data by sampling the generated acceleration data,
      identify foot strike data of the sampled acceleration data,
      identify a local minimum of the sampled acceleration data collected prior to the foot strike data, and
      determine foot strike characteristic data corresponding to the foot strike data based on an acceleration value at the local minimum.

2. The fitness tracking system of claim 1, wherein the monitoring device is permanently fixed to the shoe.

3. The fitness tracking system of claim 2, wherein:
   the shoe includes a sole portion and an upper portion extending from the sole portion,
   the monitoring device includes a housing that is fixed in position relative to the sole portion, and
   the monitoring device is located at a midfoot region of the sole portion.

4. The fitness tracking system of claim 3, wherein the controller is located in the housing of the monitoring device.

5. The fitness tracking system of claim 1, further comprising:
a personal electronic device including the controller and a display screen configured to display the foot strike characteristic data,
wherein the personal electronic device and the monitoring device are configured for wireless transmission of data.

6. The fitness tracking system of claim 1, further comprising:
determining a movement efficiency variable corresponding to a level of fatigue of the user based on the sampled acceleration data.

7. The fitness tracking system of claim 1, wherein:
the accelerometer is a multi-axis accelerometer,
only one axis of the multi-axis accelerometer is configured to generate the acceleration data, and
the one axis of the multi-axis accelerometer corresponds to a vertical axis.

8. A method of operating a fitness tracking system to determine foot strike characteristic data of a user of the fitness tracking system, the method comprising:
generating acceleration data with an acceleration sensor mounted to a foot of the user, the acceleration data corresponding to acceleration of the foot;
collecting sampled acceleration data by sampling the generated acceleration data;
identifying foot strike data of the sampled acceleration data;
identifying a local minimum of the sampled acceleration data collected prior to the foot strike data; and
determining foot strike characteristic data corresponding to the foot strike data based on an acceleration value at the local minimum.

9. The method of claim 8, further comprising:
determining jerk value data as a numerical derivative of the sampled acceleration data;
identifying the local minimum within an evaluation window;
identifying an end point of the evaluation window as a first jerk value data point of the jerk value data corresponding to a maximum absolute value of jerk prior to the foot strike data; and
identifying a start point of the evaluation windows as a second jerk value data point of the jerk value data located a predetermined number of data points prior to the first jerk value data point.

10. The method of claim 9, wherein identifying the local minimum comprises:
identifying pairs of jerk value data points of the jerk value data that correspond to local minima of acceleration within the evaluation window; and
identifying a selected pair of jerk value data points as a pair of the identified pairs of jerk value data points having a lowest sum of absolute values as compared to a sum of absolute values of each other identified pair of jerk value data points,
wherein the local minimum of the sampled acceleration data corresponds to the selected pair of jerk value data points.

11. The method of claim 9, wherein the predetermined number of data points is from ten to fifty.

12. The method of claim 9, wherein the predetermined number of data points is based on at least one of a cadence of the user, a ground contact time of the user, a speed of the user, and a stride length of the user.

13. The method of claim 8, wherein the foot strike characteristic data corresponds to a foot strike pattern of the foot, the method further comprising:
identifying the foot strike characteristic data having a value greater than a first predetermined threshold as heel-strike data;
identifying the foot strike characteristic data having a value less than a second predetermined threshold as forefoot-strike data; and
identifying the foot strike characteristic data having a value less than or equal to the first predetermined threshold and greater than or equal to the second predetermined threshold as midfoot-strike data.

14. The method of claim 8, further comprising:
permanently embedding the acceleration sensor in a shoe worn by the user.

15. The method of claim 8, further comprising:
normalizing the foot strike characteristic data to have a value ranging from zero to one.

16. The method of claim 8, wherein the foot strike characteristic data corresponds to a foot strike pattern of the foot, the method further comprising:
generating the acceleration data during a workout of the user; and
determining a change in the foot strike pattern during the workout based on the foot strike characteristic data.

17. A method of operating a fitness tracking system to determine foot strike characteristic data of a user of the fitness tracking system, the method comprising:
generating acceleration data with an acceleration sensor mounted to a foot of the user, the acceleration data corresponding to acceleration of the foot;
collecting sampled acceleration data by sampling the generated acceleration data;
identifying foot strike data of the sampled acceleration data; and
determining foot strike characteristic data corresponding to the foot strike data based on acceleration data generated prior to the foot strike data.

18. The method of claim 17, further comprising:
determining jerk value data as a numerical derivative of the sampled acceleration data;
identifying an end point of an evaluation window as a first jerk value data point of the jerk value data corresponding to a maximum absolute value of jerk prior to the foot strike data;
identifying a start point of the evaluation windows as a second jerk value data point of the jerk value data located a predetermined number of data points prior to the first jerk value data point; and
determining the foot strike characteristic data based on the sampled acceleration data within the evaluation window.

19. The method of claim 18, wherein the predetermined number of data points is based on at least one of a cadence of the user, a ground contact time of the foot, a speed of the user, and a stride length of the user.

20. The method of claim 17, wherein the foot strike characteristic data corresponds to a foot strike pattern of the foot, the method further comprising:
identifying the foot strike characteristic data having a value greater than a first predetermined threshold as heel-strike data;
identifying the foot strike characteristic data having a value less than a second predetermined threshold as forefoot-strike data; and identifying the foot strike characteristic data having a value less than or equal to the first predetermined threshold and greater than or equal to the second predetermined threshold as midfoot-strike data.

* * * * *